United States Patent [19]

Borland et al.

[11] Patent Number: 5,081,293
[45] Date of Patent: Jan. 14, 1992

[54] PROCESS FOR PREPARING SOLID BETAINES

[75] Inventors: James E. Borland; Jeffrey W. Perine; Joe D. Sauer; Kim R. Smith, all of Baton Rouge, La.

[73] Assignee: Ethyl Corporation, Richmond, Va.

[21] Appl. No.: 652,616

[22] Filed: Feb. 8, 1991

[51] Int. Cl.$^5$ ............................................. C07C 229/00
[52] U.S. Cl. ..................... 562/575; 562/553; 562/567
[58] Field of Search ......................... 562/553, 567, 575

[56] References Cited

U.S. PATENT DOCUMENTS

| | | | |
|---|---|---|---|
| 2,082,275 | 6/1937 | Daimler | 562/575 |
| 2,129,264 | 9/1938 | Downing | 562/575 |
| 2,564,507 | 8/1951 | Schaeffer | 562/575 |
| 2,800,502 | 7/1957 | Vassel | 562/575 |
| 3,480,665 | 11/1969 | Nagy | 562/575 |
| 3,555,079 | 1/1971 | Murumo | 260/501.13 |
| 3,649,677 | 3/1972 | Morris | 562/575 |
| 3,954,845 | 5/1976 | Martinsson | 562/567 |
| 4,832,871 | 5/1989 | Bade | 252/546 |

FOREIGN PATENT DOCUMENTS 1185111 3/1970 United Kingdom.

OTHER PUBLICATIONS

Nandakumar, "Journal of the Oil Technologists' Association of India," vol. 11(2), pp. 31–34 (1979).

*Primary Examiner*—Michael L. Shippen
*Attorney, Agent, or Firm*—Patricia J. Hogan

[57] ABSTRACT

Betaines are produced in solid form by reacting the corresponding quaternary ammonium ester with a base, such as sodium hydroxide, in a polar aprotic solvent in which the betaine is substantially insoluble, the ester being the product obtained by reacting a tert-amine, such as an N-alkyldimethylamine, with an alkyl haloalkanoate. The haloalkanoate is preferably a compound corresponding to the formula $X(CH_2)_nCOOZ$ in which X is chloro, bromo, or iodo; Z is an alkyl group containing 1–6 carbons; and n is an integer of 1–6. A preferred solvent for use in the process is 2-butanone.

15 Claims, No Drawings

PROCESS FOR PREPARING SOLID BETAINES

FIELD OF INVENTION

This invention relates to a process for preparing solid betaines from quaternary ammonium esters.

BACKGROUND

As disclosed in British Patent 1,185,111 (Morris) and U.S. Pat. No. 2,082,275 (Daimler et al.), U.S. Pat. No. 3,555,079 (Marumo et al.), and U.S. Pat. No. 4,832,871 (Bade), it is known that tert-amines can be quaternized with haloalkanoate salts in water or a polar protic organic solvent to prepare betaines in solution form, most commonly as 30–35% active aqueous solutions. Nandakumar et al., *Journal of the Oil Technologists' Association of India,* Volume 11(2), pp. 31–34 (1979) show that it is also known that a betaine solution can be obtained by reacting the tert-amine with a haloalkanoate ester to form a quaternary ammonium ester and then reacting the intermediate with a base to convert it to the corresponding betaine.

Solid betaines have the advantages over betaine solutions that they can be transported at lower costs and offer more flexibility in the formation of products from the betaines. It is possible to recover solid betaines from the solutions described above, but it would be preferable to be able to prepare the betaines directly in solid form.

SUMMARY OF INVENTION

It has now been found that betaines can be produced in solid form by the reaction of a base with the quaternary ammonium ester resulting from the quaternization of a tert-amine with an alkyl haloalkanoate when the reaction is conducted in a polar aprotic solvent in which the betaine is substantially insoluble.

DETAILED DESCRIPTION

As evidenced by the variety of types of tert-amines which have been quaternized with haloalkanoates in the past, the particular tert-amine used in preparing a quaternary ammonium ester of the invention is not critical. It may be, e.g., any of the tert-amines of Morris, Daimler et al., Marumo et al., and Bade, the teachings of all of which are incorporated herein by reference.

The tert-amines which are generally most valuable to employ in the reaction are those in which at least one of the N-substituents is an alkyl or hydroxyalkyl group and the remaining N-substituents are aliphatic or cyclic organic groups which may be hydrocarbyl or non-hydrocarbyl in nature, e.g., alkyl, hydroxyalkyl, polyoxyethylene, alkylamidoalkyl, phenyl, or benzyl, including those in which an alkyl or hydroxyalkyl group is attached to a nitrogen which is a member of a heterocyclic ring, such as a morpholine ring.

Among the preferred tert-amines are the compounds corresponding to the formula RR'R"N in which R is a linear or branched-chain alkyl group containing 6–22 carbons, more preferably a primary alkyl group containing 8–18 carbons; R' is methyl, ethyl, or 2-hydroxyethyl; and R" is independently selected from methyl, ethyl, 2-hydroxyethyl, and linear and branched-chain alkyl groups containing 6–22 carbons. These tert-amines may be used alone or in combination to provide, e.g.:

(1) a single RR'R"N amine in which R is either a linear or a branched-chain alkyl group containing a given number of carbons, (2) a mixture of RR'R"N amines in which the R of one component of the mixture is a linear alkyl group containing a given number of carbons and the R of another component of the mixture is a branched-chain alkyl group containing the same number of carbons, (3) a mixture of RR'R"N amines in which the R of one component of the mixture is a linear alkyl group containing a given number of carbons and the R of another component of the mixture is a linear alkyl group containing a different number of carbons, (4) a mixture of RR'R"N amines in which the R of one component of the mixture is a linear alkyl group containing a given number of carbons, the R of another component is a branched-chain alkyl group containing the same number of carbons, and the R of another component of the mixture is a linear or branched-chain alkyl group containing a different number of carbons, etc.

The most preferred of these tert-amines are those in which at least a majority of alkyl groups in the tert-amine or tert-amine mixture are linear and R' and R" are independently selected from methyl, ethyl, and 2-hydroxyethyl, especially those in which both R' and R" are methyl.

The haloalkanoate which is reacted with the tert-amine to form the quaternary ammonium ester is an alkyl ester of an omega-haloalkanoic acid in which the halo substituent is chloro, bromo, or iodo. These haloalkanoates are compounds wherein neither the size nor degree of linearity of the alkyl or alkanoic moiety is critical and they thus include compounds in which both moieties are small or large or in which one is small and the other large and in which both moieties are linear or branched or in which one is linear and the other branched. However, most commonly both the alkyl and the alkanoic moieties are moieties containing up to about 30 carbons; and it is preferred that any branching in the alkanoic moiety be confined to carbons other than the carbon to which the halo substituent is attached, since any branching on that carbon could be expected to slow the reaction significantly.

Exemplary of the alkyl haloalkanoates that can be used are the methyl, ethyl, propyl, isopropyl, butyl, isobutyl, pentyl, hexyl, octyl, 2-ethylhexyl, decyl, dodecyl, eicosyl, and triacontyl esters of chloroacetic, chloropropionic, chlorobutyric, chloropentanoic, chlorohexanoic, chloroheptanoic, chloro-betaethylhexanoic, and corresponding bromo- and iodoalkanoic acids. The preferred haloalkanoates are compounds corresponding to the formula $X(CH_2)_nCOOZ$ in which X is chloro, bromo, or iodo; Z is a linear or branched-chain alkyl group containing 1–6 carbons; and n is an integer of 1–6. Ordinarily the most preferred alkyl haloalkanoate is ethyl chloroacetate.

The amount of haloalkanoate employed to quaternize the tert-amine is generally at least the stoichiometric amount.

The base employed to convert the quaternary ammonium ester to the betaine may be any of the bases conventionally used in such reactions, usually the hydroxide of a Group IA or IIA metal, such as lithium, sodium, potassium, rubidium, cesium, beryllium, magnesium, calcium, strontium, or barium; or aluminum hydroxide.

It is ordinarily used in the stoichiometric amount to effect complete reaction, and the preferred base is generally sodium hydroxide. Although it may be utilized in virtually any form, e.g., as a powder, pellets, or aqueous or alcoholic solution, the more dilute solutions, i.e., those containing less than about 25% of the base, are not very desirable for use in the process because of the objective of preparing the betaine in solid form. The large amount of water contributed by a dilute aqueous solution of the base could solubilize the betain and/or cause foaming if later concentration of the product were to become necessary.

Both the tert-amine/alkyl haloalkanoate reaction and the quaternary ammonium ester/base reaction are conducted in solvents. It is critical that the solvent employed in the latter reaction be a polar aprotic solvent in which the betaine is substantially insoluble, at least at room temperature; and, to facilitate recovery of the quaternary ammonium ester for use in the base reaction, or to permit effecting the base reaction in the reaction mixture resulting from the synthesis of the quaternary ammonium ester, it is desirable to conduct the tert-amine/alkyl haloalkanoate reaction in the same type of solvent.

Organic solvents in which the betaines and quaternary ammonium esters are substantially insoluble, at least at room temperature, include, e.g., ketones such as 2-propanone, 2-butanone, 3-methyl-2-butanone, 2-pentanone, and 3-pentanone; nitriles such as acetonitrile, propionitrile, butyronitrile, and isobutyronitrile; cyclic ethers such as tetrahydrofuran, tetrahydropyran, and dioxane; sulfoxides such as dimethylsulfoxide; amides such as hexamethylphosphoramide, N-methylpyrrolidone, dimethylformamide, dimethylacetamide, and diethylformamide; and esters such as methyl benzoate, phenyl propionate, ethyl acetate, and other alkyl alkanoates in which both the alkyl and alkanoic moieties contain about 2-6 carbons.

Any of the aforementioned solvents is suitable for use in the quaternary ammonium ester synthesis when that ester is to be recovered from its synthesis reaction mixture before being subjected to reaction with the base. However, since the efficiency of the betaine synthesis would be considerably reduced if a reactive solvent were used for the reaction between the quaternary ammonium ester and the base, only those solvents which would be inert in such a reaction should be used in that reaction or in the quaternary ammonium ester synthesis when the base reaction is to be effected in the reaction mixture resulting from the synthesis of the ester. Thus, the amides, nitriles, and esters, which would not be inert in the base reaction, should not be used therein; but the other aforementioned solvents are quite suitable. The preferred solvents are the ketones, especially 2-butanone.

The process of the invention is conducted by contacting the base with the quaternary ammonium ester in the presence of the solvent and allowing the base to react with the ester and remove the esterifying group. This contact may be conveniently effected by adding the base to a mixture of the quaternary ammonium ester and the solvent or by passing the mixture over a bed of the base.

Whether the ester/solvent mixture which is contacted with the base is the reaction mixture resulting from the synthesis of the quaternary ammonium ester or a mixture of a solvent with a quaternary ammonium ester which has been recovered from such a reaction mixture, the quaternary ammonium ester is preferably prepared by combining the tert-amine with the haloalkanoate in a solvent in which the corresponding quaternary ammonium ester is substantially insoluble, at least at room temperature, and allowing quaternization of the tert-amine to occur. The quaternary ammonium ester thus prepared can then be left in its synthesis reaction mixture when it is desired to use the same solvent for the base reaction; or it can be recovered from the reaction mixture, e.g., by filtration, and mixed with a different solvent for use in the base reaction.

Although the quaternization and base reactions can be effected at room temperature and subatmospheric or atmospheric pressure, it is ordinarily preferred to use an elevated temperature and/or superatmospheric pressure to speed the reactions. The preferred temperatures are in the range of about 50°-150° C., most conveniently the reflux temperatures of the reaction mixtures; and the preferred pressures are about 0.1-2.1 MPa. The time required for the reactions depends, of course, on the temperatures and pressures used, varying from days at room temperature and atmospheric pressure to less than an hour at reflux temperatures and 0.4 MPa.

Because of the insolubility of the betaine product in the reaction solvent, it is easily recovered as a solid by filtration. The solid thus recovered is a betaine product having high activity; and its activity can be increased to an even higher level, in fact to as high as 100%, by removing some-to-all of the salt by-product of the base reaction and any remaining solvent, if desired.

The invention is advantageous as a convenient means of preparing solid betaines which can be used in the same applications as conventional betaine solutions, e.g., in the production of soaps and shampoos, but which offer more flexibility in the formation of products because of not having any solvent associated therewith and which are also more economical to transport.

The following examples are given to illustrate the invention and are not intended as a limitation thereof.

EXAMPLE I

A suitable reaction vessel was charged with 100 g of N-tetradecyldimethylamine, 53 g of ethyl chloroacetate, and 500 mL of 2-butanone. The reaction mixture was heated to reflux with stirring and refluxed for eight hours to quaternize the amine. Then 50 g of 98% active sodium hydroxide pellets were added to the mixture, and stirring with reflux was continued for an additional hour. HPLC analysis showed that conversion of the quaternary ammonium ester to betaine was complete, and the mixture was filtered to remove inorganic material, cooled in an ice bath, and filtered again to provide the betaine product as a white solid.

EXAMPLE II

A suitable reaction vessel was charged with 0.20 mol of N-hexadecyldimethylamine, 0.21 mol of methyl chloroacetate, and 200 mL of 2-butanone. The reaction mixture was heated to reflux with stirring and refluxed for six hours to quaternize the amine. Then 12.5M aqueous sodium hydroxide was added dropwise over five minutes to introduce 0.22 mol of sodium hydroxide. The resultant mixture was stirred at reflux (80° C.) for ten minutes, cooled to 40° C., and vacuum-filtered through Whatman #1 paper to remove the sodium chloride by-product. The filtrate was chilled to below 0° C. to precipitate the betaine, which was then collected by vacuum filtration through Whatman #2 paper and dried on a vacuum pump overnight to yield 45.4 g of N-hexadecyl-N,N-dimethylglycine as a white powder.

What is claimed is:

1. In a process for preparing a betaine by reacting the corresponding quaternary ammonium ester with a base, the ester being the product obtained by reacting a tert-amine with an alkyl haloalkanoate, the improvement which comprises conducting the quaternary ammonium ester/base reaction in a polar aprotic solvent in which the betaine is substantially insoluble.

2. The process of claim 1 wherein the base is a Group IA or IIA metal hydroxide.

3. The process of claim 2 wherein the base is sodium hydroxide.

4. The process of claim 1 wherein the tert-amine is a compound corresponding to the formula RR'R"N in which R is an alkyl group containing 6–22 carbons; R' is methyl, ethyl, or 2-hydroxyethyl; and R" is independently selected from methyl, ethyl, 2-hydroxyethyl, and alkyl groups containing 6–22 carbons.

5. The process of claim 4 wherein R is a primary alkyl group containing 8–18 carbons and R' and R" are independently selected from methyl, ethyl, and 2-hydroxyethyl.

6. The process of claim 5 wherein R' and R" are methyl.

7. The process of claim 4 wherein R and R" are independently selected from primary alkyl groups containing 8–18 carbons.

8. The process of claim 7 wherein R' is methyl.

9. The process of claim 1 wherein the haloalkanoate is a compound corresponding to the formula $X(CH_2)_nCOOZ$ in which X is chloro, bromo, or iodo; Z is an alkyl group containing 1–6 carbons; and n is an integer of 1–6.

10. The process of claim 9 wherein the haloalkanoate is ethyl chloroacetate.

11. The process of claim 1 wherein the quaternary ammonium ester which is reacted with the base is an ester which has been recovered from its synthesis reaction mixture before being contacted with the base in the presence of the polar aprotic solvent.

12. The process of claim 1 wherein the tert-amine is reacted with the haloalkanoate to form the quaternary ammonium ester in the polar aprotic solvent, and the base is then added to the resultant mixture and reacted with the quaternary ammonium ester.

13. The process of claim 12 wherein the reactions are conducted at a temperature of about 50°–150° C.

14. The process of claim 13 wherein the temperature is the reflux temperature of the reaction mixture.

15. The process of claim 14 which is conducted under superatmospheric pressure.

* * * * *